United States Patent [19]

Afonso et al.

[11] Patent Number: 5,382,572

[45] Date of Patent: Jan. 17, 1995

[54] ALKYL AND ACYL SUBSTITUTED QUINOLINES

[75] Inventors: Adriano Afonso, West Caldwell; Jay Weinstein, Upper Montclair; Margaret J. Gentles, Bloomfield, all of N.J.

[73] Assignee: Schering Corporation, Kenilworth, N.J.

[21] Appl. No.: 30,187

[22] PCT Filed: Sep. 6, 1991

[86] PCT No.: PCT/US91/06251

§ 371 Date: Mar. 1, 1993

§ 102(e) Date: Mar. 1, 1993

[87] PCT Pub. No.: WO 92/04326

PCT Pub. Date: Mar. 19, 1992

Related U.S. Application Data

[63] Continuation-in-part of Ser. No. 579,744, Sep. 7, 1990, abandoned.

[51] Int. Cl.⁶ .................... C07D 215/22; A61K 31/37
[52] U.S. Cl. ......................................... 514/82; 514/63; 514/312; 514/432; 514/456; 514/682; 546/14; 546/23; 546/155; 549/23; 549/283; 549/285; 568/328
[58] Field of Search ............................ 514/312, 63, 82; 546/155, 14, 25, 156

[56] References Cited

U.S. PATENT DOCUMENTS

| | | | |
|---|---|---|---|
| 4,547,511 | 10/1985 | Eriksoo et al. | 514/312 |
| 4,735,951 | 5/1988 | Clemence | 514/312 |
| 4,851,409 | 7/1989 | Young et al. | 514/312 |
| 4,963,576 | 10/1990 | Oku et al. | 546/152 |
| 5,175,151 | 12/1992 | Afonso et al. | 514/63 |
| 5,179,093 | 1/1993 | Afonso et al. | 514/312 |
| 5,179,107 | 1/1993 | Afonso et al. | 514/312 |
| 5,190,956 | 3/1993 | Afonso et al. | 514/312 |

FOREIGN PATENT DOCUMENTS

| | | | |
|---|---|---|---|
| 578536 | 8/1976 | Switzerland | |
| 92/04326 | 3/1992 | WIPO | 546/155 |

OTHER PUBLICATIONS

Derwent Abstract J90005-752-B (1990).
Derwent Abstract J89035-827-B (1980).
Yoshizaki Chem. Abstr., vol. 113, entry 211864Z (1990).
Schaefer, Chem. Abstr., vol. 109 entry 170249Z (1988).
Chem. Abstr., vol. 114 (1991), entry 143242P.
Schaefer et al. Chem. abstr. vol. 109 Entry 170249 (1988).

*Primary Examiner*—Donald G. Daus
*Attorney, Agent, or Firm*—Eric S. Dicker; John J. Maitner; Matthew Boxer

[57] ABSTRACT

Compounds useful as antiviral agents against DNA-containing viruses, such as herpes group viruses, are disclosed. The compounds are represented by Formula 1.0:

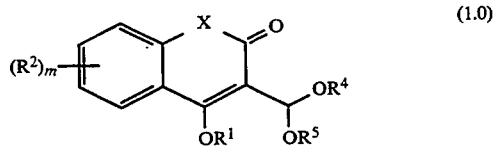

and their pharmaceutically acceptable salts and solvates;

wherein:

(A) X is selected from the group consisting of N—$R^3$, O, S, and $C(R^3)_2$;

(B) $R^3$ is selected from H and a range of substituents;

(C) $R^1$ is an etherifying or esterifying group;

(D) $R^2$ is selected from a range of substituents;

(E) m is 0 or an integer from 1 to 4; and (F) $R^4$ and $R^5$ are the same and are selected from alkyl and acyl groups;

together with the pharmaceutically acceptable salts of the compounds of Formula 1.0 that are acidic or basic.

Pharmaceutical compositions containing compounds represented by Formula 1.0 are disclosed. Also disclosed are methods of treating a viral infection using compounds represented by Formula 1.0.

14 Claims, No Drawings

ALKYL AND ACYL SUBSTITUTED QUINOLINES

The present application is the United States national application corresponding to International Application No. PCT/U.S. 91/06253, filed Sept. 6, 1991 and designating the United States, which PCT application is in turn a continuation-in-part of U.S. application Ser. No. 07/579744, filed Sept. 7, 1990, now abandoned, the benefit of which applications are claimed pursuant to the provisions of 35 U.S.C. §§120, 363 and 365(C).

BACKGROUND

This invention relates to compounds having antiviral activity, pharmaceutical compositions thereof, and methods of treatment utilizing the compositions. In particular, this invention is related to compounds having antiviral activity against viruses of the herpes group, pharmaceutical compositions containing the compounds, and methods of treating viruses of the herpes group using the pharmaceutical compositions.

There are four separate viruses of the herpes group which infect and cause disease in humans. These are (1) herpes simplex virus 1 and 2 (HSV-1 and HSV-2, respectively); (2) cytomegalovirus (CMV); (3) varicel-lazoster virus (VZ); and (4) Epstein-Barr virus (EB). Examples of diseases associated with herpes simplex virus infection include herpes labialis, genital herpes (herpes progenitalis), neonatal herpes, herpetic keratitis, eczema herpeticum, disseminated herpes, occupational herpes, herpetic gingivostomatitis, meningitis (aseptic), and encephalitis.

CMV is widespread in humans and numerous other mammals. The great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

The great majority of serious cases due to CMV infection come from recurring infections in immunocompromised patients, such as transplant patients and cancer patients. It has been estimated that silent CMV infections have occurred in a majority of humans by the time adulthood is reached.

VZ virus is associated with chicken-pox (varicella) and shingles (zoster) in humans.

EB virus is quite common and causes glandular fever; it is also believed to cause the genetic damage that leads to Burkitt's lymphoma.

Examples of drugs used to treat herpes infections include: (1) IUDR (5'-iodo-2'-deoxyuridine); (2) Ara-C (1-[beta-D-arabinofuranosyl]-cytosine); (3) Ara-A (9-beta-D-arabinofuranosyladenine); and (4) Acyclovir (9-[(2-hydroxyethoxy)methyl]guanine). Also Haines et al. (U.S. Pat. No. 4,757,088 issued Jul. 12, 1988) disclose that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

In view of current interest in the art for finding useful antiviral agents, in particular, useful agents against herpes group viruses, any new compounds exhibiting antiviral activity would be a welcome contribution to the art. This invention provides such a contribution.

SUMMARY OF THE INVENTION

This invention provides compounds which are useful as antiviral agents against DNA-containing viruses such as herpes group viruses. In particular, the compounds of this invention are useful against HSV-1 and HSV-2 and may also prove useful against CMV and EB.

The compounds of this invention are advantageous over known viral compounds because they inhibit early events in viral replication.

One embodiment of this invention provides compounds of Formula 1.0

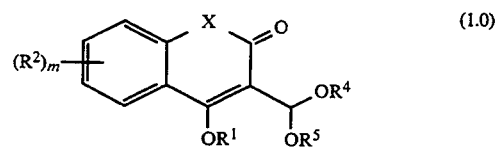

(1.0)

wherein:

(A) X is selected from the group consisting of N—$R^3$, O, and S;

(B) $R^3$ is selected from the group consisting of:
(1) alkyl;
(2) aralkyl;
(3) aryl;
(4) substituted aryl;
(5) alkaryl;
(6) alkyl heteroaryl;
(7) aryloxyalkoxyalkyl;
(8) —$(CH_2)_a R^{16}$ wherein a is an integer of 1 to 6 and $R^{16}$ is selected from the group consisting of —C(O)O$R^{17}$, —O$R^{17}$, —$R^{17}$, and —N($R^{17}$)$_2$, wherein each $R^{17}$ can be the same or different and is selected from the group consisting of alkyl, alkenyl and H;
(9) H; and
(10) —O$R^{18}$ wherein $R^{18}$ is selected from the group consisting of H, alkyl—optionally substituted with OH, SH, $NH_2$ and/or halogen—, alkaryl, alkenyl, and heteroaryl;

(C) $R^1$ is selected from the group consisting of:
(1) alkyl;
(2) haloalkenyl wherein the halogen atoms are selected from the group consisting of F, Cl, Br and I;
(3) —$(CH_2)_a NR^6 R^7$ wherein a is an integer from 1 to 6, and $R^6$ and $R^7$ are the same or different and are selected from the group consisting of H and alkyl; and
(4) acyl having the formula —C(O)$R^8$ wherein $R^8$ is selected from the group consisting of H, alkyl, aryl, alkaryl, alkenyl, heteroaryl, and substituted alkyl;

(D) Each $R^2$ for each m is independently selected from the group consisting of:
(1) alkyl;
(2) alkoxy;
(3) aryloxy;
(4) aryl;
(5) aralkyloxy;
(6) halogen atoms selected from the group consisting of F, Cl, Br and I;

(7) —O—CO—$R^{10}$ wherein $R^{10}$ is alkyl—optionally substituted with OH, SH, $NH_2$ and/or halogen—, alkaryl, alkenyl, and heteroaryl;

(8) —N($R^{11}$)$_2$ wherein each $R^{11}$ is independently selected from the group consisting of H, alkyl, aryl, and $R^{12}$C(O)— wherein $R^{12}$ is as above defined.

(9) —OH;

(10) —$CH_2OH$;

(11) —COOH;

(12) —COO$R^{13}$, wherein $R^{13}$ is selected from the group consisting of alkyl and aryl;

(13) —$SO_3H$;

(14) —$SO_2NHR^{14}$, wherein $R^{14}$ is selected from the group consisting of alkyl; aryl; and H;

(15) —$PO_3H$;

(16) —PO(O$R^{15}$)$_2$, wherein $R^{15}$ is selected from the group consisting of alkyl and aryl;

(17) —$OPO_3H$;

(18) —OP(O$R^{15}$)$_2$ wherein $R^{15}$ is as above defined;

(19) —$CF_3$; and

(20) $CONH_2$;

(E) m is 0 or an integer from 1 to 4; and (F) $R^4$ and $R^5$ are the same and are selected from the group consisting of:

(1) alkyl; and (2) acyl having the formula —C(O)$R^8$ wherein $R^8$ is selected from the group consisting of H, alkyl, aryl, alkaryl, alkenyl, heteroaryl, and substituted alkyl;

together with the pharmaceutically acceptable salts of the compounds of Formula 1.0 that are acidic or basic.

Another embodiment of this invention provides pharmaceutical compositions comprising an effective amount of a compound of this invention and a pharmaceutically acceptable carrier or excipient. Preferably the compound is selected from the group of compounds represented by Formulas 1.1 to 1.19 below. The pharmaceutical compositions are useful in treating viral infections in a patient in need of such treatment. Examples of treatable viral infections include the DNA-containing viruses such as the herpes viruses discussed above (e.g., HSV-1, HSV-2, CMV, VZ, EB, and the like).

In yet another embodiment this invention provides a method of treating a patient having a viral infection by administering to such a patient an effective amount of a compound of this invention. Generally, in the method of treatment the compound which is administered is administered as one of the pharmaceutical compositions of this invention. Examples of viral infections treatable in accordance with the methods of this invention include the DNA-containing viruses such as the herpes viruses discussed above (e.g., HSV-1, HSV-2, CMV, VZ, EB, and the like).

DETAILED DESCRIPTION OF THE INVENTION

When used herein, the terms listed below have the scope indicated, unless indicated otherwise.

Acyl—represents a group having the formula —C(O)$R^8$ wherein $R^8$ is selected from the group consisting of H, alkyl, aryl, alkaryl, alkenyl, alkynyl, cycloalkyl, cycloalkenyl, heteroaryl, and substituted alkyl. Representative examples of acyl groups include $CH_3C(O)$—, $CH_3CH_2C(O)$—, $CH_3CH_2CH_2C(O)$—, phenyl—C(O)—, pyridyl—C(O)—, and the like.

Alkaryl—represents an aryl group, as defined below, in which an alkyl group, as defined below, is substituted for one of the aryl H atoms. The aryl group may contain additional substituents selected from the group consisting of halogen atoms (i.e, Cl, Br, F, and/or I), alkoxy, alkyl, and amino. Representative examples include $CH_3$phenyl—, $CH_3CH_2$phenyl—, and the like.

Alkenyl—represents straight and branched aliphatic hydrocarbon groups having at least one carbon-to-carbon double bond and preferably having from 2 to 6 carbon atoms. Preferably the alkenyl substituent has from 1 to 2 double bonds. Representative examples include vinyl, allyl, butenyl and the like.

Alkoxy—represents an alkyl radical attached to a molecule through an oxygen atom (—O—alkyl). Representative examples include methoxy, ethoxy and the like.

Alkyl—represents straight or branched aliphatic hydrocarbon groups which contain from 1 to 6 carbon atoms. Representative examples include methyl, ethyl, propyl and the like.

Heteroaryl alkyl—represents a heteroaryl group, as defined below, substituting an alkyl group, as defined above. Representative examples include pyridylmethyl, furylmethyl and the like.

Haloalkenyl—represents an alkenyl group, as defined above, wherein one or more hydrogen atoms is replaced by a halogen atom. The halogen atoms can be anywhere along the molecule; however, haloalkenyl radicals having the halogen atom at the terminal position are preferred. Preferably only one halogen atom is present in the haloalkenyl group. The halogen atoms are selected from the group consisting of F, Cl, Br, and I; and preferably from the group consisting of Cl and Br. Most preferably the halogen atom is Br. Representative examples include bromobutenyl, bromopropenyl and the like.

Aryloxyalkoxyalkyl—represents a group wherein an aryloxy group substitutes an alkoxy group which in turn substitutes another alkyl group and the first oxygen atom is attached to the aryl group at a ring carbon atom. Alkoxy is as defined above and aryl is as defined below. The aryl group may contain additional substituents selected from the group consisting of halogen atoms (i.e., Cl, Br, F, and/or I), alkoxy, alkyl, and amino. Representative examples include phenoxypropoxymethyl, phenoxyethoxymethyl and the like.

Alkynyl—represents a straight or branched aliphatic hydrocarbon group having at least one carbon-to-carbon triple bond, and having from 3 to 8 carbon atoms with from 3 to 6 carbon atoms being preferred. Representative examples include propynyl, butynyl and the like.

Aralkyl—represents an alkyl group as defined above in which an aryl group as defined below is substituted for one of the alkyl hydrogen atoms. Representative examples include —$CH_2$phenyl, —$CH_2CH_2$phenyl, 4-t-butyldimethylsilyloxybenzyl and the like.

Aralkoxy—represents an aralkyl group as defined above, which is attached to a molecule through an oxygen atom (aralkyl—O—). The aryl group may contain additional substitutents selected from the group consisting of halogen atoms (i.e., Cl, Br, F, and/or I), alkoxy, alkyl, and amino. Representative examples include benzyloxy, phenylethoxy, and the like.

Aryl—represents a mono- or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of halogen atoms (i.e., Cl, Br, F, and/or I), alkoxy, alkyl, and amino.

Aryloxy—represents an aryl group as defined above, which is attached through an oxygen atom (aryl—O—). The aryl group may contain additional substituents selected from the group consisting of halogen atoms (i.e., Cl, Br, F, and/or I), alkoxy, alkyl, and amino. Representative examples include phenoxy, naphthyloxy, and the like.

Cycloalkenyl—represents a carbocyclic ring having from 5 to 7 carbon atoms and at least one carbon-to-carbon double bond in the ring, such as cyclopentenyl, cyclohexenyl, cycloheptenyl, and the like.

Cycloalkyl—represents a saturated carbocyclic ring having from 3 to 7 carbon atoms. Representative examples include cyclopropyl, cyclohexyl, and the like.

Heteroaryl (including the heteroaryl portion of heteroarylmethyl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 3-N-methylpyrrolyl and the like.

Substituted alkyl—represents an alkyl group, as defined above, wherein one or more of the alkyl H atoms is replaced with a group selected from the group consisting of alkyl, aryl, heteroaryl, —OH, —O—alkyl, —NH$_2$, —N(alkyl)$_2$ wherein each alkyl group is the same or different, —S—alkyl, —C(O)O—alkyl, —C-(O)H, —NHC(:NH)NH$_2$, —C(O)NH$_2$, —OC(O)NH$_2$, NO$_2$ and —NHC(O)—alkyl, wherein alkyl, aryl, and heteroaryl are as above defined. Representative examples of groups include hydroxyethyl, aminoethyl, mercaptoethyl, trifluoromethyl, halogen and the like.

Substituted aryl—represents an aryl group, as defined above, wherein one or more of the H atoms attached to the ring carbon atoms is replaced by a group independently selected from the group consisting of halo, alkyl, hydroxy, alkoxy, phenoxy, amino, alkylamino, and dialkylamino. Preferred substituted aryl groups are substituted phenyl groups.

Also, as used herein, the following abbreviations have the following meanings unless indicated otherwise: C(O) represents C=O; Ac represents CH$_3$C(O); Ph represents phenyl, and Ar represents aromatic.

In the compounds of this invention X is preferably NR$^3$.R$^1$ is preferably selected from the group consisting of acyl and alkyl. R$^4$ and R$^5$ are preferably acyl and most preferably they are the same; when R$^1$ is also acyl, it also is preferably the same as R$^4$ and R$^5$. Preferably R$^2$ is selected from the group consisting of:
(1) —CH$_3$;
(2) —OCH$_3$;
(3) —OCOCH$_3$;
(4) —OCH$_2$-phenyl;
(5) Cl;
(6) F; and
(7) I.

Preferably R$^3$ is selected from the group consisting of:
(1) —OH$_3$;
(2) —C$_6$H$_{13}$;
(3) —C$_7$H$_{15}$;
(4) —CH$_2$-phenyl;

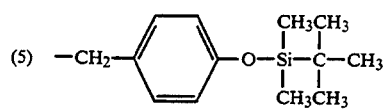

(6) -phenyl

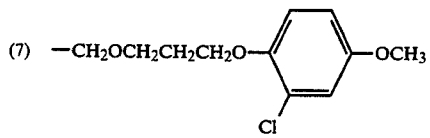

(8) —CH$_2$CO$_2$CH$_2$CH=CH$_2$; and
(9) —CH$_2$CO$_2$CH$_3$.

Also, in the compounds of this invention X is preferably NR$^3$.

In one group of preferred compounds of Formula 1.0, X is selected from O, S and NR$^3$, wherein R$^3$ is selected from from the group consisting of:
(1) —CH$_3$;
(2) —C$_6$H$_{13}$;
(3) —C$_7$H$_{15}$;
(4) —CH$_2$-phenyl;

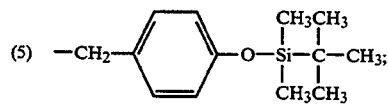

(6) phenyl;

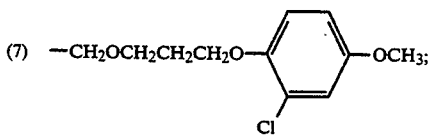

(8) —CH$_2$CO$_2$CH$_2$CH—C H$_2$; and
(9) —CH$_2$CO$_2$CH$_3$;

R$^2$ is selected from the group consisting of:
(1) —OH$_3$;
(2) —OCH$_3$;
(3) —OCOCH$_3$;
(4) —OCH$_2$-phenyl;
(5) Cl;
(6) F; and
(7) I; and
m is 0, 1 or 2;

R$^4$ and R$^5$ are selected from the group consisting of acetyl, 1-oxopentyl, 1-oxopropyl, and methyl; and R$^1$ is selected from the group consisting of methyl, acetyl, 1-oxopentyl, and 1-oxopropyl.

In a particularly preferred group of these compounds, R$^3$ is selected from the group consisting of:
(1) —CH$_3$;
(2) —C$_6$H$_{13}$;
(3) —C$_7$H$_{15}$;
(4) —CH$_2$-phenyl;
(5) —CH$_2$CO$_2$CH$_2$CH=CH$_2$;
(6) -phenyl; and (7) 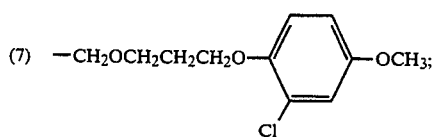
and R² is selected from the group consisting of:
(1) —CH₃;
(2) —OCOCH₃; and
(3) —OCH₂-phenyl; and
m is 0, 1 or 2.
Compounds of this invention include compounds selected from the group consisting of Formulae 1.1 to 1.19 (designated above each chemical formula) in the following Table:
TABLE OF CHEMICAL COMPOUNDS
(1.1)
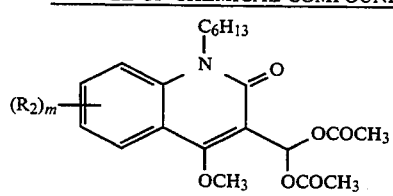
(1.2)
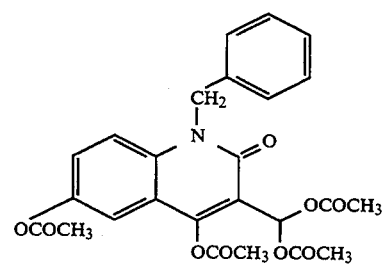
(1.3)
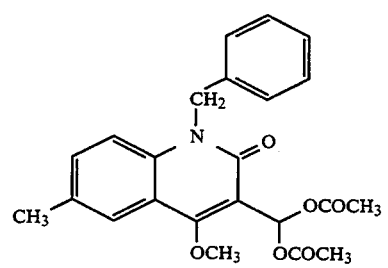
(1.4)
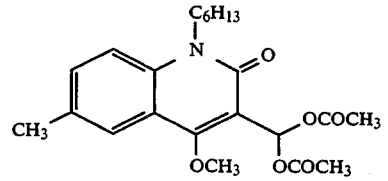
(1.5)
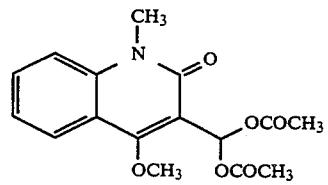
-continued
TABLE OF CHEMICAL COMPOUNDS
(1.6)
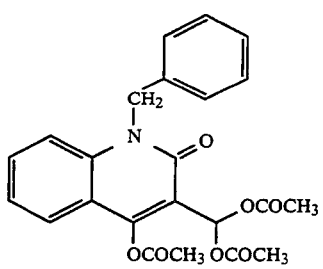
(1.7)
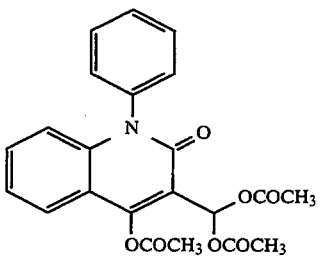
(1.8)
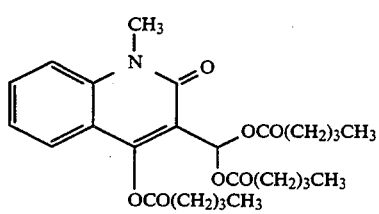
(1.9)
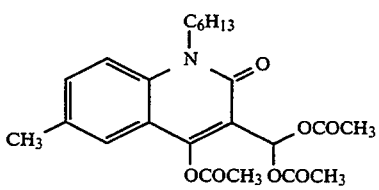
(1.10)
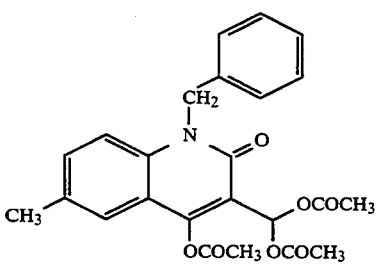
(1.11)
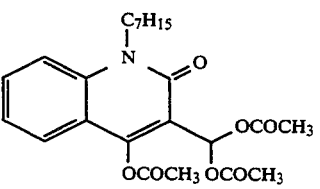
(1.12)
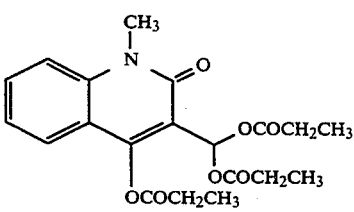

-continued
TABLE OF CHEMICAL COMPOUNDS

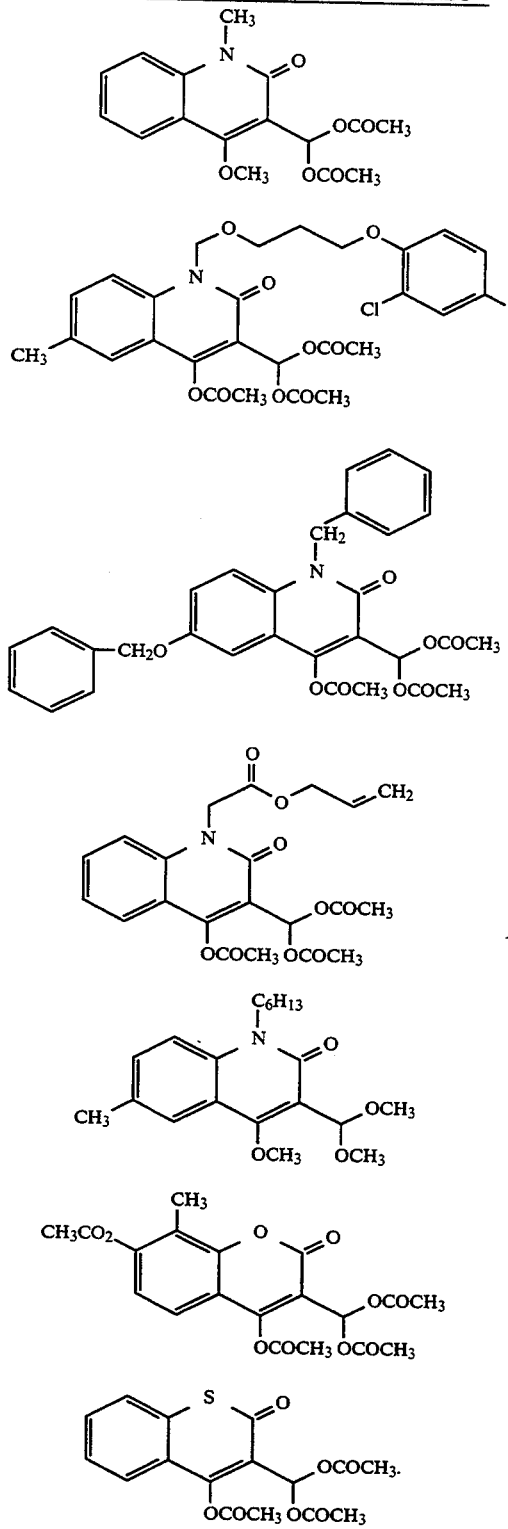

Preferably compounds of this invention are selected from the group consisting of Formulas 1.1, 1.3, 1.4, 1.5, and 1.14.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms. e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum. salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

The compounds of Formula 1.0 can be prepared by the processes described below, wherein the substituents are as described above, unless indicated otherwise. Those skilled in the art will appreciate that in the processes described below the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techniques well known in the art such as distillation, column chromatography, recrystallization, and the like.

The invention therefore provides a process for the preparation of a compound of Formula 1.0 defined above, which comprises:

(a) for the preparation of a compound of Formula 1.0 wherein $R^1$ is not acyl, and $R^4=R^5=$acyl or alkyl, the reaction of a compound of the formula A:

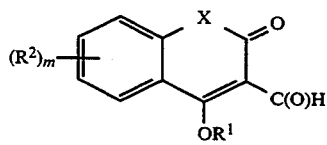

wherein $R^2$, X and m are as defined above, and $R^1$ is as defined for Formula 1.0 except that it is not acyl, with an alcohol $R^4OH$ or with a carboxylic anhydride $(R^8CO)_2O$, wherein $R^4$ and $R^8$ are as defined above, in the presence of an appropriate catalyst; or (b) for the preparation of a compound of Formula 1.0 wherein $R^1=R^4=R^5=$acyl, the reaction of a compound of the formula A:

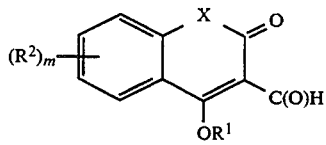

wherein $R^2$, X and m are as defined above and $R^1$=H, with a carboxylic anhydride $(R^8CO)_2O$, wherein $R^8$ is as defined above, in the presence of an appropriate catalyst.

Catalysts that are appropriate for use in the above process (a) include strong acids, for example strong organic acids such as sulphonic acids, especially touene-p-sulfonic acid, and mineral acids such as chlorsulfonic acid or sulfuric acid. In process (b), a basic catalyst such as a tertiary amine, e.g. pyridine or triethylamine, is used. The reaction is effected in the presence of a solvent, which may for example be an excess of the anhydride $(R^8CO)_2O$ or alcohol $R^4OH$ in process (a) or an excess of the basic catalyst such as pyridine or triethylamine in process (b).

Thus, compounds of Formula 1.0 wherein $R^1$=$R^4$=$R^5$=acyl, can be prepared by reacting compounds of Formula A wherein $R^1$=H $(R^8CO)_2O$ (wherein $R^8$ is as defined above) in the presence of an acid catalyst, according to general procedures known in the art (see, for example J. March, Advanced Organic Chemistry, cited above, Chapter 6.57, the disclosure of which is incorporated herein by reference thereto).

Compounds of Formula 1.0, wherein $R^1$ is not acyl but is otherwise as defined above for Formula 1.0, and $R^4$=$R^5$=alkyl, can be prepared by reacting compounds of Formula A wherein $R^1$ is not acyl but is as otherwise defined above for Formula 1.0 with an alcohol $R^4OH$ in the presence of an acid catalyst, according to general procedures known in the art (see, for example, J. March, Advanced Organic Chemistry, John Wiley and Sons, Publishers, 1985, Chapter 6.6, the disclosure of which is incorporated herein by reference thereto).

The starting materials of the Formula A can be prepared by one of the following reaction Schemes I and II:

Scheme I shows how the starting materials of the Formula 1.0 can be prepared from readily available starting materials; in this Scheme, the radicals $R^1$, $R^2$, and X, and m, are as defined for Formula 1.0, and $R^{19}$ is an esterifying group, preferably a lower alkyl group such as ethyl or methyl. Compounds of the Formulae 2.1, 2.2, 2.3 and 2.4 are quinolinones when X is $NR^3$:

SCHEME I

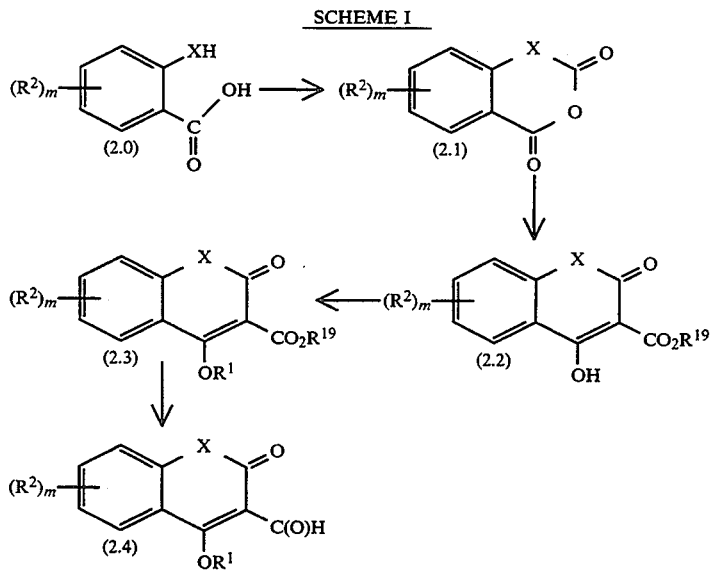

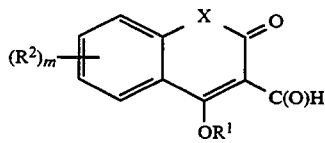

with an acylating agent such as a carboxylic acid anhydride $(R^8CO)_2O$ (at least 3 molar equivalents and preferably up to 10, e.g., about 5), in the presence of an organic base such as pyridine (6 to 20 molar equivalents). The reaction is carded out at room temperature and is usually complete in a few hours.

Compounds of Formula 1.0 wherein $R^1$ is not acyl but is otherwise as defined above for Formula 1.0, and $R^4$=$R^5$=acyl, can be prepared by reacting compounds of Formula A wherein $R^1$ is not acyl but is otherwise as defined above for Formula 1.0 with an anhydride The conversions of a compound of Formula 2.0 into a compound of the Formula 2.1, and of a compound of the Formula 2.1 into a compound of the Formula 2.2, represent reactions well known to those skilled in the art; see for example G. M. Coppola et al., Synthesis, 505 (1980), the disclosure of which is incorporated herein by reference thereto.

In the first step, a suitable 2-substituted benzoic acid 2.0 in aqueous 2N HCl is reacted with trichloromethyl chloroformate to form a compound 2.1, which is an isatoic anhydride when X is NH or $NR^3$. The 2-substituted benzoic acid 2.0 will have the appropriate $R^2$ substituent group(s) to give the desired end product.

When X in the compound of Formula 1.0 is to be $NR^3$, wherein $R^3$ is other than hydrogen, but is NH in the isatoic anhydride of the formula 2.1, then this compound of the Formula 2.1 can be reacted with a suitable $R^3$-halide (wherein $R^3$ is as above defined) to produce the desired $R^3$-substituted isatoic anhydride of the formula 2.1. This is also disclosed by G. M. Coppola et al., *Synthesis*, 505 (1980).

In the second step, the compound of formula 2.1 is reacted with the anion derived from a malonate ester to produce the compound of the formula 2.2 (which is a quinolinone when X is $NR^3$). $R^{19}$ is ethyl when diethyl malonate is used in the reaction.

In the third step, the compound of the formula 2.2 can be reacted with suitable reagents to produce the compound of the formula 2.3 having an ether group at C-4, when this is desired. This reaction can be carried out by standard methods for the preparation of ethers, for example by reaction of an alkali metal salt of the compound of the Formula 2.2 with a halide $R^1.Hal$, or by reaction of the compound of the Formula 2.2 with a diazoalkane such as diazomethane,in a suitable organic solvent.

In the final step, the ester group at C-3 of the compound of the Formula 2.3 is reduced to provide the the compound of the Formula 2.4 with the required aldehyde group at C-3, for example by treating a solution of the compound of the Formula 2.3 in an appropriate organic solvent with a molar equivalent of di-isobutylaluminum hydride at low temperature.

The starting materials of the Formula 2.4 can also be prepared by Scheme II, wherein the compounds of the Formula 2.3 can be prepared by the method given in Scheme I:

SCHEME II

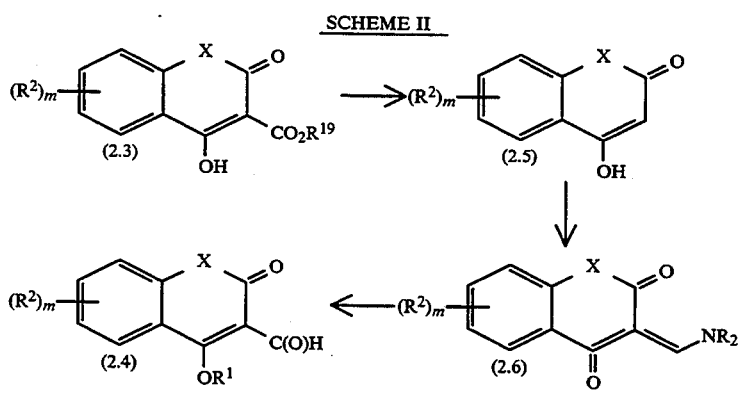

In the first step of Scheme II, the compound of the Formula 2.3 is decarboxylated to produce the compound of the Formula 2.5, for example, by procedures well known in the art; see e.g. G. M. Coppola et al, *J. Org. Chem.*, 4.1, 825 (1976), the disclosure of which is incorporated herein by reference thereto.

In the second step, the compound of the Formula 2.5 is convened into the disubstituted aminomethylenedione of the Formula 2.6 (wherein R is any suitable organic group but is preferably a lower alkyl group such as ethyl or methyl), for example by reacting the compound of the Formula 2.5 with dimethyl formamide dimethylacetal in a low-boiling organic solvent.

In the third step, the compound of the Formula 2.6 is hydrolyzed to the 3-aldehyde-4-hydroxy compound of the Formula 2.4, for example under aqueous acidic conditions.

The compounds of this invention can be administered in any number of conventional dosage forms, e.g., topical, oral, parenteral, rectal, transdermal, inhalation and the like. Oral or rectal dosage forms include capsules, tablets, pills, powders, and suppositories cachets. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, e.g., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended for conversion, shortly before use, to liquid form preparations for either oral or parenteral administration. Such, liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended for conversion to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration; for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration, by employing an antivirally effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small amounts until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to about 100mg/kg.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following examples are illustrative only and should not be construed as limiting the invention in any way. Those skilled in the art will appreciate that variations are possible which are within the spirit and scope of the appended claims.

In the Examples, Ar represents an aromatic group.

PREPARATION A

Preparation of 1-Benzyl-4-Hydroxy-6-Methyl-2(1H)-Quinolinone

Step (1): Preparation of 6-Methyl-Isatoic Anhydride

A solution of 2-amino-5-methyl-benzoic acid (4.5 gm) in 2N HCl (15 ml) and water (35 ml) was stirred vigorously while trichloromethyl chloroformate (5.6 gin) was added dropwise. The reaction was stirred for an additional 10 mins and then filtered; the solid cake was washed with water and dried under reduced pressure to give 6-methyl-isatoic anhydride as a light yellow powder (4.7 gm).

Step (2): Preparation of 1-Benzyl-6-Methyl-Isatoic Anhydride

A solution of 6-methyl-isatoic anhydride (4.5 gm) in DMF (30 ml) was added dropwise to a stirred suspension of 60% sodium hydride (1.0 gm) in DMF (20 ml) under nitrogen atmosphere. The reaction was then warmed to 45° C. and stirred until hydrogen evolution ceased. It was then cooled and a solution of benzyl bromide (4.4 gm) in DMF (10 ml) was added slowly.

Stirring was continued for one hour at room temperature and the solution was then evaporated under reduced pressure at 45° C. The resulting solid was suspended in methylene chloride, the insoluble inorganic solid was removed by filtration and the filtrate was evaporated to give 1-benzyl-6-methyl-isatoic anhydride as a crystalline solid.

Step (3): Preparation of 1-Benzyl-3-Ethoxycarbonyl-4-Hydroxy-6-Methyl-2(1H)-Quinolinone A solution of diethyl melonate (4.07 gm)in dimethyl acetamide (DMA) (10 ml) was added dropwise to a stirred suspension of 60% sodium hydride (1.01 gm) in the same solvent (10 ml), under a nitrogen atmosphere, in an oil bath at 25° C. After hydrogen evolution ceased, the temperature was raised to 80° C. while adding a solution of 1-benzyl-6-methyl-isatoic anhydride (4.5 gm) in DMA (50 ml). After carbon dioxide evolution ceased, the reaction mixture was heated at 120° C. for 17 hours and then was concentrated under reduced pressure to a volume of 25 ml. and then was diluted with water (50 ml). The milky solution was washed with ether, the aqueous layer was acidified with mineral acid to pH3 and the resulting crystalline product 1-benzyl-3-ethoxycarbonyl-6-methyl-2(1H)-quinolinone was isolated by filtration.

Step (4): Preparation of 1-Benzyl-4-Hydroxy-6-Methyl-2(1H)-Quinolinone

The product from Step (3) was dissolved in 2N sodium hydroxide (150 ml) and the solution was refluxed for 4 hours. Then the solution was cooled and acidified with mineral acid to pH3. The solid was filtered, dried and crystallized from ethyl acetate/hexane to give 1-benzyl-4-hydroxy-6-methyl-2(1H)-quinolinone (4.0 gm). That the expected product was obtained was confirmed by the spectral data: MS: m/e 265 (M.+); NMR (DMSO): $\delta$2.32 (s, 3H, $CH_3$—Ar), 5.43 (s, 2H, $CH_2$—Ar), 5.96 (s, 1H, =CH—), 11.48 (s, 1H, OH) ppm.

PREPARATION B

Preparation of 1-Methyl-3-Formyl-4-Hydroxy-2(1H)-Quinolinone

Step (1): Preparation of 1-methyl-3-dimethylaminomethylene-(1H)-quinolin-2,4-dione A suspension of 1-methyl-4-hydroxy-2(1H)-quinolinone (1.0 gm) in dimethyl formamide dimethyl acetal (5 ml) and methylene chloride (2.0 ml) was refluxed for 1 hour. The resulting dark orange solution was evaporated under reduced pressure to give 1-methyl-3-dimethylamino-methylene-(1H)-quinolin-2,4-dione.

Step (2): Preparation of 1-methyl-3-formyl-4-hydroxy-2(1H)-quinolinone

The product from Step (1) was dissolved in distilled water (50 ml) by gentle warming and then the resulting solution was filtered. The clear filtrate was cooled in an ice bath and acidified to pH3 with mineral acid. The resulting crystalline precipitate was washed with water and dried to give 1-methyl-3-formyl-4-hydroxy-2(1H)-quinolinone. That the expected product was obtained was confirmed by the spectral data: MS: m/e 203 (M.+); NMR (CDCl$_3$): $\delta$3.6 (s, 3H, NCH$_3$), 10.28 (s, 1H, CHO) ppm.

EXAMPLE 1

Preparation of 1-Hexyl-3-Diacetyloxymethyl-4-Methoxy-2(1H)-Quinolinone (Formula 1.1)

Step (1): Preparation of 1-Hexyl-Isatoic Anhydride

Following the procedure of Step (2) of Preparation A, isatoic anhydride was reacted with hexyl bromide to produce 1-hexyl-isatoic anhydride.

Step (2): Preparation of 1-Hexyl-3-Ethoxycarbonyl-4-Hydroxy-2(1H)-Quinolinone

Following the procedure set forth in Step (3) of Preparation A, 1-hexyl-isatoic anhydride was converted to 1-hexyl-3-ethoxycarbonyl-4-hydroxy-2(1H)-quinolinone.

Step (3): Preparation of 1-Hexyl-3-Formyl-4-Methoxy-2(1H)-Quinolinone

A solution of 1.6 g of 1-hexyl-3-ethoxycarbonyl-4-hydroxy-2(1H)-quinolinone in dichloromethane (20 ml) and ethanol (2 ml) was treated with excess diazomethane in ether for 10 mins and is then evaporated. The crude methylation product upon chromatography on silica gel yielded 1-hexyl-3-ethoxycarbonyl-4-methoxy-2(1H)-quinolinone (1.0 g). This product (1.0 g) in dry toluene (10 ml) was cooled to $-78°$ C. and a 1M solution of diisobutyl aluminum hydride (4.3 ml) was added dropwise in 10min. After 2.5 hours stirring at$-78°$ C. the reaction mixture was worked up by stirring with aqueous ammonium chloride/1N hydrochloric acid followed by extraction with methylene chloride. The crude reduction product was chromatographed on silica gel and crystallized from ethyl acetate/hexane to give 1-hexyl-3-formyl-4-methoxy-2(1H)-quinolinone as a crystalline solid. That the expected product was obtained was confirmed by the spectral data: MS (FAB): m/e 288 (M.++1); NMR (CDCl$_3$): $\delta$4.12 (s, 3H, OCH$_3$), 10.5 (s, 1H, CHO).

Step (4): Preparation of 1-Hexyl-3-Diacetyloxymethyl-4-Methoxy-2(1H)-Quinolinone 1-Hexyl-3-formyl-4-methoxy-2(1H)-quinolinone (Step (3) of Example 1), 0.26 g, was dissolved in acetic anhydride (1 ml) containing p-toluenesulfonic acid (0.05 g). After 4 hours the solution was diluted with ethyl acetate, washed with aqueous sodium bicarbonate, dried and evaporated under reduced pressure. The crude reaction product was chromatographed on silica gel to give 1-hexyl-3-diacetyloxymethyl-4-methoxy-2(1H)-quinolinone (Formula 1.1) as a colorless oil. That the expected product was obtained was confirmed by the spectral data: MS (CI): m/e 390 (M.$^{30}$ +1); NMR (CDCl$_3$): $\delta$2.22 (s, 6H, 2 X CH$_3$COO. ), 4.20 (s, 3H, OCH$_3$), 8.21 (s, 1H, CH(OAc)$_2$).

EXAMPLE 2

Preparation of 1-Benzyl-3-Diacetyloxymethyl-4.6-Diacetyloxy-2(1H)-Quinolinone (Formula 1.2)

Step (1): Preparation of 1-Benzyl-4-Hydroxy-6-Benzyloxy-2(1H)-Quinolinone

Following the procedure described in Steps 1–4 of Preparation A, 2-amino-5-benzyloxy-benzoic acid was converted to the title compound.

Step (2): Preparation of 1-Benzyl-4,6-Dihydroxy-2(1H)-Quinolinone

A solution of the title compound of Step (1) (2.8 g) in a mixture of methanol (180 ml) and acetic acid (75 ml) was hydrogenated at atmospheric pressure in the presence of 10% palladium-carbon (2.0 g) until no further uptake of hydrogen was observed. The reaction mixture was then filtered and the filtrate was evaporated to dryness. The solid residue was crystallized to give the title compound (1.4 g). That the expected product was obtained was confirmed by the spectral data: MS: m/e 267 (M.+).

Step (3): Preparation of 1-Benzyl-3-Diacetyloxymethyl-4,6-Diacetyloxy-2(1H)-Quinolinone Following the procedure described in Preparation B and Example 5 (below), the product from Step (2) was convened to the title compound. That the expected product was obtained was confirmed by the spectral data: MS: m/e 481 (M.+); NMR (CDCl$_3$): δ2.12 (s, 6H, 2 x CH$_3$—COO), 2.30 (s, 3H, CH$_3$COO), 2.52 (s, 3H, CH$_3$COO), 5.65 (s, 2H, CH$_2$Ph), 8.10 (s, 1H, CH(OAc)$_2$) ppm.

EXAMPLE 3

Preparation of
1-Benzyl-3-Diacetyloxymethyl-4-Methoxy-6-Methyl-2(1H)-Quinolinone (Formula 1.3)

Step (1): Preparation of 1-Benzyl-3-Formyl-4-Methoxy-6-Methyl-2(1H)-Quinolinone

A solution of 1-benzyl-3-ethoxycarbonyl-4-hydroxy-6-methyl-2(1H)-quinolinone obtained in Step (3) of Preparation A (12.4 g) in dichloromethane (50 ml) and methanol (10 ml) was treated with excess diazomethane in ether for 10 mins and was then evaporated. The crude methylation product, upon chromatography on silica gel, yielded 1-benzyl-3-ethoxycarbonyl-4-methoxy-6-methyl-2(1H)-quinolinone (11.5 g). This product (7.13 g) in dry toluene (80 ml) was cooled to −78° C. and a 1M solution of di-isobutyl aluminum hydride (30 ml) was added dropwise in 10 min. After 2.5 hours stirring at −78° C. the reaction mixture was worked up by stirring with aqueous ammonium chloride/1N hydrochloric acid followed by extraction with methylene chloride. The crude reduction product was chromatographed on silica gel and crystallized from ethyl acetate/hexane to give 1-benzyl-3-formyl-4-methoxy-6-methyl-2(1H)-quinolinone as a yellow solid (7.8 g). That the expected product was obtained was confirmed by the spectral data: NMR (CDCl$_3$): δ2.40 (s, 3H, CH$_3$), 4.18 (s, 3H, OCH$_3$), 10.58 (s, 1H, CHO); MS (FAB): m/e 308 (M.++1).

Step (2): Preparation of 1-Benzyl-3-Diacetyloxymethyl-4-Methoxy-6-Methyl-2(1H)-Quinolinone The aldehyde (0.85 g) obtained in Step (1) of Example 3 was dissolved in acetic anhydride (2 ml) containing p-toluenesulfonic acid (0.13 g). After 4 hours the solution was diluted with ethyl acetate, washed with aqueous sodium bicarbonate, dried and evaporated under reduced pressure. The crude reaction product was chromatographed on silica gel and crystallized from ethyl acetate-hexane to give 1-benzyl-3-diacetyloxy-methyl-4-methoxy-6-methyl-2(1H)-quinolinone as a white solid. That the expected product was obtained was confirmed by the spectral data: MS (CI): m/e 410 (M.++1); NMR (CDCl$_3$): δ2.18 (s, 6H, 2 x CH$_3$COO), 2.4 (s, 3H, CH$_3$), 4.15 (s, 3H, OCH$_3$), 8.15 (s, 1H, CH(OAc)$_2$) ppm.

EXAMPLE 4

Preparation of
1-Hexyl-3-Diacetyloxymethyl-4-Methoxy-6-Methyl-2(1H)-Quinolinone

Step (1): Preparation of 1-Hexyl-6-Methyl-Isatoic Anhydride

Following the procedure of Step (2) of Preparation A, 6-methyl-isatoic anhydride was reacted with hexyl bromide to yield 1-hexyl-6-methyl-isatoic anhydride.

Step (2): Preparation of 1-Hexyl-3-Ethoxycarbonyl-4-Hydroxy-6-Methyl-2(1H)-Quinolinone Following the procedure of Step (3) of Preparation A, 1-hexyl-6-methyl-isatoic anhydride was converted to 1-hexyl-3-ethoxycarbonyl-4-hydroxy-6-methyl-2(1H)-quinolinone.

Step (3): Preparation of 1-Hexyl-3-Formyl-4-Methoxy-6-Methyl-2(1H)-Quinolinone

Following the procedure of Step (1) of Example 3, 1-hexyl-3-ethoxycarbonyl-4-hydroxy-6-methyl-2(1H)-quinolinone was converted to 1-hexyl-3-formyl-4-methoxy-6-methyl-2(1H)-quinolinone. That the expected product was obtained was confirmed by the spectral data: MS (CI): m/e 302 (M.++1); NMR (CDCl$_3$): δ2.42 (s, 3H, Ar—CH$_3$), 4.10 (s, 3H, OCH$_3$), 10.50 (s, 1 H, CHO).

Step (4): Preparation of 1-Hexyl-3-Diacetyloxymethyl-4-Methoxy-6-Methyl-2(1H)-Quinolinone Following the procedure set forth in Step (2) of Example 3, 1-hexyl-3-formyl-4-methoxy-6-methyl-2(1H)-quinolinone was converted to 1-hexyl-3-diacetyloxymethyl-4-methoxy-6-methyl-2(1H)-quinolinone. That the expected product was obtained was confirmed by the spectral data: MS (CI): m/e 404 (M.++1); NMR(CDCl$_3$): δ2.18 (s, 6H, 2 x CH$_3$COO),2.42 (s, 3H, Ar—CH$_3$), 8.10 (s, 1H, CH(OAc)$_3$).

EXAMPLE 5

Preparation of
1-Methyl-3-Diacetyloxymethyl-4-Acetyloxy-2(1H)-Quinolinone (Formula 1.5)

A solution of 1-methyl-3-formyl-4-hydroxy-2(1H)-quinolinone (6.0 gm) in pyridine (50 ml) and acetic anhydride (10 ml) was allowed to stand at 10° C. for 24 hours. The resulting suspension was diluted with ethyl acetate (150 ml), stirred for 1 hour and filtered. The crystalline product was washed with ether and dried under reduced pressure to give 1-methyl-3-diacetyloxymethyl-4-acetyloxy-2(1H)-quinolinone (8.0 gm). That the expected product was obtained was confirmed by the spectral data: MS: m/e 347 (M.+); NMR (CDCl$_3$): δ2.12 (s, 6H, 2 x CH$_3$COO), 2.52 (s, 3H, CH$_3$COO), 3.75 (s, 3H, NCH$_3$), 8.10 (s, 1H, CH(OAc)$_2$) ppm.

EXAMPLE 6

Preparation of
1-Benzyl-3-Diacetyloxymethyl-4-Acetyloxy-2(1H)-Quinolinone (Formula 1.6)

Step (1): Preparation of 1-Benzyl-Isatoic Anhydride

Following the procedure set forth in Step (2) of Preparation A, isatoic anhydride was reacted with benzyl bromide to give 1-benzyl-isatoic anhydride.

Step (2): Preparation of 1-Benzyl-3-Ethoxycarbonyl-4-Hydroxy-2(1H)-Quinolinone

Following the procedure of Step (3) of Preparation A, 1-benzyl-isatoic anhydride was converted to 1-benzyl-3-ethoxycarbonyl-4-hydroxy-2(1H)-quinolinone.

Step (3): Preparation of 1-Benzyl-4-Hydroxy-2(1H)-Quinolinone

Following the procedure of Step (4) of Preparation A, 1-benzyl-3-ethoxycarbonyl-4-hydroxy-2(1H)-quinolinone was converted to 1-benzyl-4-hydroxy-2(1H)-quinolinone. That the expected product was obtained was confirmed by the spectral data: MS: m/e 251 (M.+); NMR (DMSO): 85.47 (s, 2H, CH$_2$—Ar), 6.03 (s, 1H, =CH), 11.6 (s, 1H, OH) ppm.

Step (4): Preparation of 1-Benzyl-3-Formyl-4-Hydroxy-2(1H)-Quinolinone

Following the procedure of Preparation B, 1-benzyl-4-hydroxy-2(1H)-quinolinone was converted to 1-benzyl-3-formyl-4-hydroxy-2(1H)-quinolinone. That the expected product was obtained was confirmed by the spectral data: MS (FAB): m/e 370 (M.+ +1); NMR (DMSO): δ5.50 (s, 2H, CH$_2$—Ar), 10.18 (s, 1 H, CHO) ppm.

Step (5): Preparation of 1-Benzyl-3-Diacetyloxymethyl-4-Acetyloxy-2(1H)-Quinolinone Following the procedure of Example 5, 1-benzyl-3-formyl-4-hydroxy-2(1H)-quinolinone was acetylated to give 1-benzyl-3-diacetyloxymethyl-4-acetyloxy-2(1H)-quinolinone. That the expected product was obtained was confirmed by the spectral data: MS (CI): m/e 424 (M.+ +1); NMR (DMSO): δ2.09 (s, 6H, 2 x CH$_3$COO), 2.54 (s, 3H, CH$_3$COO), 5.58 (s, 2H, CH$_2$—Ar), 7.96 (s, 1H, CH(OAc)$_2$) ppm.

EXAMPLE 7

Preparation of 1-Phenyl-3-Diacetyloxymethyl-4-Acetyloxy-2(1H)-Quinolinone (Formula 1.7)

Step (1): Preparation of 1-Phenyl-4-Hydroxy-2(1H)-Quinolinone

Following the procedure of Preparation A, N-phenylamino-benzoic acid was converted to 1-phenyl-4-hydroxy-2(1H)-quinolinone. That the expected product was obtained was confirmed by the spectral data: MS: m/e 237 (M.+); NMR (DMSO): δ5.92 (s, 1H, =CH), 11.60 (s, 1 H, OH) ppm.

Step (2): Preparation of 1-Phenyl-3-Formyl-4-Hydroxy-2(1H)-Quinolinone

Following the procedure of Preparation B, 1-phenyl-4-hydroxy-2(1H)-quinolinone was converted to 1-phenyl-3-formyl-4-hydroxy-2(1H)-quinolinone. That the expected product was obtained was confirmed by the spectral data: MS: m/e 265 (M.+); NMR (DMSO): δ10.08 (s, 1H, CHO) ppm.

Step (3): Preparation of 1-Phenyl-3-Diacetyloxymethyl-4-Acetyloxy-2(1H)-Quinolinone Following the procedure of Example 5, 1-phenyl-3-formyl-4-hydroxy-2(1H)-quinolinone was convened to 1-phenyl-3-diacetyloxymethyl-4-acetyloxy-2(1H)-quinolinone. That the expected product was obtained was confirmed by the spectral data: MS (CI): m/e 410 (M.+ +1); NMR (DMSO): δ2.10 (s, 6H, 2 x CH$_3$COO), 2.58 (s, 3H, CH$_3$COO), 7.90 (s, 1H, CH(OAc)$_2$) ppm.

EXAMPLE 8

Preparation of 1-Methyl-3-[Di-(1-Oxopentyloxy)methyl]-4-(1-Oxopentyloxy)-2(1H)-Quinolinone (Formula 1.8)

Following the procedure of Example 5, 1-methyl-3-formyl-4-hydroxy-2(1H)-quinolinone (obtained from Preparation B) was acylated with pentanoic anhydride to give 1-methyl-3-[di-(1-oxopentyloxy)methyl]-4-(1-oxopentyloxy)-2(1H)-quinolinone. That the expected product was obtained was confirmed by the spectral data: MS: m/e374 (M.+); NMR (CDCl$_3$): δ0.90 (t, 6H, 2 x CH$_3$CH$_2$), 1.02 (t, 3H, CH$_3$CH$_2$), 1.33 (m, 4H, CH$_2$), 1.84 (m, 2H, CH$_2$), 2.35 (m, 4H, CH$_2$CO), 2.80 (t, 2H, CH$_2$CO), 3.73 (s, 3H, NCH$_3$), 8.06 (s, 1H, [CH$_3$(CH$_2$)$_3$COO]$_2$CH) ppm.

EXAMPLE 9

Preparation of 1-Hexyl-3-Diacetyloxymethyl-4-Acetyloxy-6-Methyl-2(1H)-Quinolinone (Formula 1.9)

Following the procedure of Example 5, 1-hexyl-3-formyl-4-hydroxy-6-methyl-2(1H)-quinolinone was acetylated to produce 1-hexyl-3-diacetyloxymethyl-4-acetyloxy-6-methyl-2(1H)-quinolinone. That the expected product was obtained was confirmed by the spectral data: NMR (DMSO): δ0.86 (t, 3H, CH$_3$CH$_2$), 1.3–1.6 (br, 8H, (CH$_2$)$_4$), 2.05 (s, 6H, 2 x CH$_3$COO), 2.40 (s, 3H, CH$_3$—Ar), 2.50 (s, 3H, CH$_3$COO), 4.25 (m, 2H, NCH$_2$), 7.90 (s, 1 H, CH(OAc)$_2$) ppm.

The 1-hexyl-3-formyl-4-hydroxy-6-methyl-2(1H)-quinolinone was obtained by following Steps (2) to (4) of Preparation A wherein hexyl bromide was reacted with 6-methyl-isatoic anhydride to produce 1-hexyl-4-hydroxy-6-methyl-2(1H)-quinolinone. Then the 1-hexyl-4-hydroxy-6-methyl-2(1H)-quinolinone was converted to 1-hexyl-3-formyl-4-hydroxy-6-methyl-2(1H)-quinolinone following the procedure of Preparation B.

EXAMPLE 10

Preparation of 1-Benzyl-3-Diacetyloxymethyl-4-Acetyloxy-6-Methyl-2(1H)-Quinolinone (Formula 1.10)

The title compound was obtained by starting with the product of Preparation A and following the procedure of Preparation B and Example 5. That the expected product was obtained was confirmed by the spectral data: MS: m/e 437 (M.+).

EXAMPLE 11

Preparation of 1-Heptyl-3-Diacetyloxymethyl-4-Acetyloxy-2(1H)-Quinolinone (Formula 1.11)

Step (1): Preparation of 1-Heptyl-3-Formyl-4-Hydroxy-2(1H)-Quinolinone

Following the procedure set forth in Preparation B, 1-heptyl-4-hydroxy-2(1H)-quinolinone was converted to 1-heptyl-3-formyl-4-hydroxy-2(1H)-quinolinone. That the expected product was obtained was confirmed by the spectral data: MS: m/e 287 (M.+); NMR (DMSO): δ0.88 (t, 3H, CH$_3$—CH$_2$), 4.20 (m, 2H, N—CH$_2$), 10.10 (s, 1H, CHO) ppm.

1-Heptyl-4-hydroxy-2(1H)-Quinolinone was obtained by following the procedures set forth in Steps (2) to (4) of Preparation A wherein heptyl bromide was reacted with isatoic anhydride.

Step (2): Preparation of 1-Heptyl-3-Diacetyloxymethyl-4-Acetyloxy-2(1H)-Quinolinone Following the procedure of Example 5, 1-heptyl-3-formyl-4-hydroxy-2(1H)-quinolinone was acetylated to produce 1-heptyl-3-diacetyloxymethyl-4-acetyloxy-2(1H)-quinolinone. That the expected product was obtained was confirmed by the spectral data: MS: m/e 372

(M —$CH_3COO$); NMR (DMSO): δ0.88 (t, 3H, $CH_3CH_2$), 2.05 (S, 6H, 2 x $CH_3COO$), 2.52 (s, 3H, $CH_3COO$), 4.25 (m, 2H, $NCH_2$), 7.90 (s, 1 H, $CH(OAc)_2$) ppm.

EXAMPLE 12

Preparation of 1-Methyl-3-[Di-(1-Oxopropoxy)]methyl-4-(1-Oxopropoxy)-2(1H)-Quinolinone (Formula 1.12)

Following the procedure of Example 5, 1-methyl-3-formyl-4-hydroxy-2(1H)-quinolinone (from Preparation B) was acylated with propanoic anhydride to give 1-methyl-3-[di-(1-oxopropoxy)]methyl-4-(1-oxopropoxy)-2(1H)-quinolinone. That the expected product was obtained was confirmed by the spectral data: MS (CI): m/e 390 (M.$^+$+1); NMR ($CDCl_3$): δ1.14 (t, 6H, 2 x $CH_3CH_2$), 1.38 (t, 3H, $CH_3CH_2$), 2.39 (m, 4H, 2 x $CH_2CO$), 2.83 (q, 2H, $CH_3CH_2CO$), 3.74 (s, 3H, $NCH_3$), 8.10 (s, 1 H, $(CH_3CH_2COO)_2CH$) ppm.

EXAMPLE 13

Preparation of 1-Methyl-3-Diacetyloxymethyl-4-Methoxy-2(1H)-Quinolinone (Formula 1.13)

Step (1): Preparation of 1-Methyl-3-Formyl-4-Methoxy-2(1H)-Quinolinone

Following the procedure of Step (1) of Example 3, 1-methyl-3-ethoxycarbonyl-4-hydroxy-2(1H)-quinolinone was converted to 1-methyl-3-formyl-4-methoxy-2(1H)-quinolinone. That the expected product was obtained was confirmed by the spectral data: MS (EI): m/e 217 (M.$^+$); NMR ($CDCl_3$): δ3.70 (s, 3H, $NCH_3$), 4.15 (s, 3H, $OCH_3$), 10.50 (s, 1H, CHO).

1-Methyl-3-ethoxycarbonyl-4-hydroxy-2(1H)-quinolinone was obtained according to J. Org. Chem. p. 829, 1976. It could also be obtained by following Procedure A.

Step (2): Preparation of 1-Methyl-3-Diacetyloxymethyl-4-Methoxy-2(1H)-Quinolinone Following the procedure of Example 5, 1-methyl-3-formyl-4-methoxy-2(1H)-quinolinone was acetylated to give 1-methyl-3-diacetyloxymethyl-4-acetyloxy-2(1H)-quinolinone. That the expected product was obtained was confirmed by the spectral data: MS (CI): m/e 320 (M.$^+$+1); NMR ($CDCl_3$): δ2.15 (s, 6H, $CH_3COO—$), 3.82 (s, 3H, $NCH_3$), 4.12 (s, 3H, $OCH_3$), 8.14 (s, 1H, $CH(OAc)_2$).

EXAMPLE 14

Preparation of 1-[3-(2-Chloro-4-Methoxyphenoxy)propoxymethyl]-3-Diacetyloxymethyl-4-Acetyloxy-2(1H)-Quinolinone (Formula 1.14)

Step (1): Preparation of 1-[3-(2—Chloro-4-Methoxyphenoxy)propoxy-methyl]-4-Hydroxy-2-(1 H)-Quinolinone A solution of 2-chloro-4-methoxyphenol (15.5 gm)in DMF (20 ml) was added to a suspension of 60% sodium hydride (4 gm) in DMF (10 ml). This was followed by the addition of a solution of 3-chloropropyl benzoate (15.5 gm) in DMF (20 ml). The solution was heated at 80° C. for 20 hours, then diluted with ethyl acetate, then washed with water, then dried and then evaporated. The crude product was dissolved in a 1:1 mixture of methanol/THF (40 ml) to which 10% sodium hydroxide (50 ml) was added. The mixture was refluxed for 3 hours, then diluted with ethyl acetate, then washed with water and then evaporated. The crude product was purified by chromatography on silica gel using 40% ethyl acetate in hexane as the eluting solvent and was then dissolved in dichloroethane (40 ml) containing paraformaldehyde (2.25 gm). The solution was cooled in an ice bath and a stream of HCl gas was bubbled through it for 3.5 hours. Then the solution was dried over magnesium sulfate and the solvent was removed under reduced pressure. The resulting 3-(2-chloro-4-methoxyphenoxy) propoxymethyl chloride and isatoic anhydride were reacted following the procedure described in steps 2–4 of Preparation A to give the title compound of Step (1). That the expected product was obtained was confirmed by the spectral data: MS: m/e 389 (M.$^+$); NMR (DMSO): δ1.9 (t, 2H, $CH_2$), 3.65 (t, 2H, $CH_2O$), 3.70 (s, 3H, $OCH_3$), 3.90 (t, 2H, $CH_2O$), 5.65 (s, 2H, $NCH_2O$), 5.84 (s, 1 H, =CH).

Step (2): Preparation of the Title Compound

Following the procedure described in Preparation B and Example 5, the product from Step 1 was converted to the title compound. That the expected product was obtained was confirmed by the spectral data: MS: m/e 561 (M.$^+$); NMR ($CDCl_3$): δ2.12 (s, H, $CH_3CO_2$), 2.51 (s, 3H, $CH_3CO_2$), 3.76 (s, 3H, $OCH_3$), 3.88 (t, 2H, $CH_2O$), 4.0 (t, 2H, $CH_2O$), 5.78 (s, 2H, $N-CH_2-O$), 8.05 (s, 1H, $CH(OAc)_2$).

EXAMPLE 15

Preparation of 1-Benzyl-3-Diacetyloxymethyl-4-Acetyloxy-6-Benzyloxy-2(1H)-Quinolinone (Formula 1.15)

The product from Step (1) of Example 2 was converted to the title compound by following the procedure described for Preparation B and Example 5. That the expected product was obtained was confirmed by the spectral data: MS: m/e 529 (M.$^+$); NMR ($CDCl_3$): δ2.10 (s, 6H, 2 x $CH_3COO$), 2.48 (s, 3H, $CH_3COO$), 5.08 (s, 2H, $CH_2Ph$), 5.50 (s, 2H, $CH_2Ph$), 8.10 (s, 1 H, $CH(OAc)_2$).

EXAMPLE 16

Preparation of 1-Allyloxycarbonylmethyl-3-Diacetyloxymethyl-4-Acetyloxy-2(1H)-Quinolinone (Formula 1.16)

Step (1): Preparation of 1-methoxycarbonyl-4-Hydroxy-2-(1H)-Quinolinone

By starting with methyl chloroacetate and isatoic anhydride and following the procedure described in Steps 2–4 of Preparation A, the title compound was obtained.

Step (2): Preparation of 1-allyloxycarbonylmethyl-4-Hydroxy-2(1H)-Quinolinone

A solution of the product from Step 1 (0.29 g) in toluene (15 ml) and allyl alcohol (10 ml) containing sulfuric acid (1 drop), was refluxed for 3 hours. The reaction mixture was then cooled, washed with water and evaporated to dryness to afford the title compound as a solid. That the expected product was obtained was confirmed by the spectral data: MS (FAB): m/e 260 (M.$^+$); NMR (DMSO)—: δ4.62 (d, 2H), 5.08 (s, 2H), 5.30 (m, 2H), 5.89 (s, 1H), 5.92 (m,1H).

Step (3): Preparation of the Title Compound

The product from Step 2 was converted to the title compound by following the procedure described in Preparation B and Example 5. That the expected product was obtained was confirmed by the spectral data:

MS (FAB): m/e 432 (M.+); NMR (CDCl$_3$): δ2.10 (s, 6H, 2 x CH$_3$COO), 2.50 (s, 3H, CH$_3$COO).

EXAMPLE 17

Preparation of 1-Hexyl-3-(Dimethoxymethyl)-4-Methoxy-6-Methyl-2(1H)-Quinolinone (Formula 1.17)

A solution of 1-hexyl-3-formyl-4-methoxy-6-methyl-2(1H)-quinolinone (Step (3) of Example 4) (0.2 g) in benzene (20 ml), containing methanol (2 ml) and p-toluenesulfonic acid (0.05 g) was refluxed for 3 hours with removal of water. The mixture was then cooled, washed with aqueous sodium bicarbonate, dried, and evaporated to give 1-hexyl-3-(dimethoxymethyl)-4-methoxy-6-methyl-2(1H)-quinolinone as an oil. That the expected product was obtained was confirmed by the spectral data: MS: m/e 347 (M.+); NMR (CDCl$_3$): δ3.50 (s, 6H, 2 x OCH$_3$), 4.10 (s, 3H, OCH$_3$), 5.72 (s, 1H, CH(OOH$_3$)$_2$).

EXAMPLE 18

Preparation of 4,7-Diacetyloxy-3-Diacetyloxymethyl-8-Methyl-2H-1-Benzopyran-2-one (Formula 1.18)

If the following procedure were followed, then the title compound would be obtained:

Step (1): Preparation of 3-Formyl-4,7-Dihydroxy-8-Methyl-2H-1-Benzopyran-2-one

Following the procedure of Preparation B, 4,7-dihydroxy-8-methyl-2H-1-benzopyran-2-one (*JACS.* 141 (1958)) is converted to 3-formyl-4,7-dihydroxy-8-methyl-2H- 1-Benzopyran-2-one.

Step(2): Preparation of 4,7-Diacetyloxy-3-Diacetyloxymethyl-8-Methyl-2H-1-Benzopyran-2-one Following the procedure of Example 5, 3-formyl-4,7-dihydroxy-8-methyl-2H-1-benzopyran-2-one is acetylated to give 4,7-diacetyloxy-3-diacetyloxymethyl-8-methyl-2H- 1-benzopyran-2-one.

EXAMPLE 19

Preparation of 3-Diacetyloxymethyl-4-Acetyloxy-2H-1-Benzothiopyran-2-one (Formula 1.19)

If the following procedure were followed, then the title compound would be obtained:

Step (1): Preparation of 3-Formyl-4-Hydroxy-2H- 1-Benzothiopyran-2-one (A) A solution of thiosalicylic acid (3.0 g) in methanol (30 ml) is cooled in an ice bath and dry hydrogen chloride is bubbled in for 15 minutes. The solution is allowed to stand at room temperature for 24 hours, and then the solution is evaporated. The resulting methyl thiosalicylate is dissolved in pyridine (20 ml) containing acetic anhydride (5 ml). After 24 hours the reaction mixture is diluted with ethyl acetate, washed several times with water, dried and evaporated. The resulting acetylthiosalicylic acid methyl ester is dissolved in dimethylformamide (20 ml), cooled to 0° C. and 60% sodium hydride (0.8 g)is added while stirring. The reaction mixture is then stirred at room temperature for 12 hours, then concentrated to half volume under reduced pressure, then diluted with water, then acidified to pH3 with mineral acid and then filtered to give 4-hydroxy-2H-1-benzothiopyran-2-one.

(B) Following the procedure of Preparation B, 4-hydroxy-2H-1-benzothiopyran-2-one (Step (1 A) of this Example) is converted to 3-formyl-4-hydroxy-2H- 1-benzothiopyran-2-one.

Step (2): Preparation of 3-Diacetyloxymethyl-4-Acetyloxy-2H-1-Benzothiopyran-2-one Following the procedure of Example 5, 3-formyl-4-hydroxy-2H-1-benzothiopyran-2-one (Step (1B) of this Example)is converted to 3-diacetyloxymethyl-4-acetyloxy-2H- 1-benzothiopyran-2-one.

BIOLOGICAL DATA

Cell and Virus Culture

HeLa and Vero cell cultures were maintained in Eagle's Minimal Essential Medium (EMEM) which was supplemented with glutamine, penicillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON 245$^{ori-}$ contains the promoter of the HSV-1 thymidine kinase (tk) gene located immediately 5' of the *E. coli* lac Z gene. In this arrangement, the tk promoter controls transcription from the bacterial gene in transient expression assays. Additionally, an SV40 polyadenylation signal is present at the 3'-end of the lac Z gene to allow for the efficient translation of the mRNA in eucaryotic cells. The expression of beta-galactosidase in a transient assay using pON 245$^{ori-}$ is dependent upon superinfection of the transfected cells with HSV. Therefore, a compound which interferes with early steps of HSV replication will also inhibit beta-galactosidase production in transfected cells. For example, see European Patent Application No. 8302149.5 filed Mar. 11, 1988 and published Sep. 14th 1988 as 282,330, the disclosure of which is incorporated herein by reference thereto.

Transient Expression of Beta-Galactosidase in Transfected Cells

HeLa cells were seeded into 96 well microtiter plates and allowed to grow to 80% confluency (approximately 35000 cells/well). One half microgram of plasmid pON 245$^{ori-}$ DNA was introduced into the cells of each well by the DEAE Dextran precipitation technique (Grahman and Van der Eb, 1973). Four to six hours later, the cells were rinsed with Hank's Balanced Salt Solution (HBSS), overlaid with 10% EMEM and incubated at 37° C. At 24 hour post-transfection, cells were rinsed, overlaid with 10% EMEM again and reincubated at 37° C. At 48 hours. post-transfection, cells were rinsed and overlaid with either EMEM containing 2% fetal calf serum (2% EMEM), 2% EM EM containing HSV-2 (strain MS, Multiplicity of Infection [moil =5 pfu/cell) or 2% EMEM containing HSV-2 and the appropriate concentration of the compound to be tested. Twenty-four hours later, the cells were harvested and assayed for beta-galactosidase activity as described below.

Beta-Galactosidase Assay

All determinations of beta-galactosidase activity were performed in 96 well microtiter plates. The intracellular level of beta-galactosidase activity in each well was determined from cell lysates of the monolayer cultures. Aliquots were assayed by incubation in the presence of beta-galactosiclase substrate, 4-methyl-umbel-liferyl-$\beta$-D-galactoside (MUG, 125 µg/ml, Sigma), for 2 hour. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an IC50 value (the concentration of compound required to reduce beta-galactosidase expression by 50%) was obtained for each compound tested.

Compound Toxicity Assay

Compounds which demonstrated a significant inhibitory activity in the HeLa cell beta-galactosidase assay were assayed for their inhibitory effect on HeLa cell translation. HeLa cells were treated with inhibitory compound for 24 hours, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 µCi of tritiated leucine (141 Cµ/mMol, Amersham Corp., Arlington Heights Ill.). After a 1 hour incubation at 36.5° C., the cells were rinsed twice with phosphate buffered saline (PBS) and lysed in 400 µl/well of 1×PBS, 0.5% sodium dodecyl sulphate (SDS). After a 10 min incubation at 36.5° C., the contents of the well were transferred to a well in a Millititer HA microfiltration plate (Millipore Corp., Bedford, Mass.). The TCA-insoluble proteins were precipitated onto the filter disc by a 10-minute-fixation with 5% TCA, followed by filtration under vacuum and three 10-minute-rinses with 95% ethanol. The filters were dried at room temperature, cut from the millititer plate and transferred to scintillation vials. TCA precipitable counts were assayed in 5 ml of Scintisol (Isolab, Akron, Ohio). The inhibitory activity of a compound was plotted versus the concentration and an IC50 value (that concentration of the compound required to decrease cellular translational activity by 50%) was derived for each compound.

Analysis of In Vivo Efficacy

The in vive assessment of anti-HSV efficacy was determined in the prophylactic guinea pig model of HSV infection described by Stansberry et al (1982). Dosing of guinea pigs comprised an initial treatment with test compound given 24 hours prior to virus infection and subsequent administration of the compound every eight hours (T.I.D.) for a total of 10 days. Test compounds were administered subcutaneously in 0.5% buffered methyl celluslose at a dose of 60 mg per kg body weight of the animal. Animals were monitored daily for the development of genital lesions and neurological symptomology, both of which were recorded and compared to the results obtained with parallel groups which received placebo or acyclovir treatment. Efficacy was evaluated for each compound by scoring the ability of the compound to ameliorate genital lesions produced by infection with HSV-2, strain MS, expressed as Maximum Lesion Scores (MLS) on a scale of 1 (least lesion) to 4 (severe lesions).

In-Vitro Anti-HSV Activity

The in vitro anti-HSV activity results are shown in Table I.

Anti-HSV activity refers to the IC50 values in the HSV-$\beta$-gal assay which measures anti-viral activity in terms of inhibition of beta-galactosidase expression. The IC50 values refer to the concentration of the compound in micrograms/milliliter needed to reduce beta-galactosidase expression by 50%.

Cytotoxicity refers to the IC50 values in the 3H-leucine (3H-Leu) incorporation. The IC50 values in this test refer to the concentration of the compound in micrograms/milliliter which reduces leucine incorporation by 50%.

TABLE I

| EXAMPLE NO. | FORMULA | ANTI-HSV ACTIVITY HSV-$\beta$-GAL ASSAY IC$_{50}$ (µg/ml) | CYTOTOXICITY $^3$H-LEU ASSAY IC$_{50}$ (µg/ml) |
|---|---|---|---|
| 1 | 1.1 | 1.4 | 6 |
| 2 | 1.2 | 3.0, 2.5* | 21.5, 3* |
| 3 | 1.3 | 3.0 | 2.7 |
| 4 | 1.4 | 3.0 | 2.5 |
| 5 | 1.5 | 4.0, 3* | 25, 25* |
| 6 | 1.6 | 4.0, 8* | 32, 37* |
| 7 | 1.7 | 4.0, 4* | 20, 18* |
| 8 | 1.8 | 5.0, 4* | 30, >10* |
| 9 | 1.9 | 6.0, 8* | 32, 37* |
| 10 | 1.10 | 7.0 | 18 |
| 11 | 1.11 | 8.0, 10* | 25, 43* |
| 12 | 1.12 | 8.0, 7* | 29, 29* |
| 13 | 1.13 | 8.0 | 18 |
| 14 | 1.14 | 9.0 | 30 |
| 15 | 1.15 | 10.0, 10* | 29, 40* |
| 16 | 1.16 | 10.0 | 43 |
| 17 | 1.17 | 5.0 | 30 |

*Repeat

In-Vivo Anti-HSV Activity

The in-vivo anti-HSV activity results are shown in Table II.

TABLE II

| FORMULA | MLS[1] | NEUROLOGICAL DYSFUNCTIONS (%)[2] |
|---|---|---|
| Placebo | 3 | 87 |
| Acyclovir | 1.5 | 50 |
| 1.3 | 1.8 | 0 |
| 1.9 | 2.5 | 75 |
| 1.5 | 1.3 | 0 |
| 1.14 | 1.8 | 12 |

[1]Maximum Lesion Scores on a scale of 1–4.
[2]Percentage animals developing loss of bladder/hindlimb control.

In-Vitro CMV Activity

The compounds represented by Formulas 1.6 and 1.14 were tested for their in-vitro activity against CMV. The assays were determined using the following protocol.

CMV Assay

Human foreskin fibroblast (HHF) cell cultures were grown in 10% EMEM. CMV (strain Towne received from Stanford University) was grown and titered in HHF cells. Plasmids pON 249 and pON 241 Δ NH$_3$, containing CMV promoter genes, were used in the $\beta$-galactosidase transient expression assay as shown above.

CMV Toxicity Assay

The tritiated leucine ($^3$H-Leu) assay was performed using HFF cells.

The results are given in Table III.

TABLE III

| FORMULA | ANTI-CMV ACTIVITY CMV-β-Gal ASSAY IC$_{50}$ (μg/ml) | CYTOTOXICITY $^3$H-LEU ASSAY IC$_{50}$ (μg/ml) |
|---|---|---|
| 1.6 | 7, 8* | 28 |
| 1.14 | 16, 18* | 50 |

The invention being thus described, it will be obvious that the same may be varied in many ways. Such variations are not to be regarded as a departure from the spirit and scope of the invention and all such modifications are included within the scope of the claims.

We claim:

1. A compound of Formula 1.0:

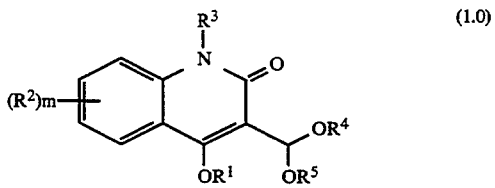

(1.0)

wherein:
(B) R$^3$ is selected from the group consisting of:
(1) alkyl;
(2) —CH$_2$—phenyl;
(3) phenyl;
(4) substituted phenyl;
(7) (2-chloro-4-methoxyphenoxy)propoxymethyl;
(8) —(CH$_2$)$_a$R$^{16}$, wherein a is an integer of 1 to 6 and R$^{16}$ is selected from the group consisting of —C(O)OR$^{17}$,— OR$^{17}$,—R$^{17}$, and—N(R$^{17}$)$_2$, wherein each R$^{17}$ can be the same or different and is selected from the group consisting of alkyl, alkenyl and H;
(9) H; and
(10) —OR$^{18}$ wherein R$^{18}$ is selected from the group consisting of H, alkyl—which may be substituted with OH, SH, NH$_2$ and/or halogen—, alkenyl;
(C) R$^1$ is selected from the group consisting of:
(1) alkyl;
(2) haloalkenyl wherein the halogen atoms are selected from the group consisting of F, Cl, Br and I;
(3) —(CH$_2$)$_a$NR$^6$R$^7$ wherein a is an integer from 1 to 6, and R$^6$ and R$^7$ are the same or different and are selected from the group consisting of H and alkyl; and
(4) acyl having the formula —C(O)R$^8$ wherein R$^8$ is selected from the group consisting of H, alkyl, phenyl, —CH$_2$—phenyl, alkenyl, and substituted alkyl;
(D) Each R$^2$ for each m is independently selected from the group consisting of:
(1) alkyl;
(2) alkoxy;
(3) phenyloxy;
(4) phenyl;
(5) phenylalkyloxy
(6) halogen atoms selected from the group consisting of F, Cl, Br and I;
(7) —O—CO—R$^{10}$ wherein R$^{10}$ is alkyl—which may be substituted with OH, SH, NH$_2$ and/or halogen—, —CH$_2$—phenyl, alkenyl;
(8) —N(R$^{11}$)$_2$ wherein each R$^{11}$ is independently selected from the group consisting of H, alkyl, and R$^{12}$C(O)— wherein R$^{12}$ is as above defined
(9) —OH;
(10) —CH$_2$OH;
(11) —COOH;
(12) —COOR$^{13}$, wherein R$^{13}$ is alkyl;
(13) —SO$_3$H;
(14) —SO$_2$NHR$^{14}$, wherein R$^{14}$ is selected from the group consisting of alkyl; and H;
(15) —PO$_3$H;
(16) —PO(OR$^{15}$)$_2$, wherein R$^{15}$ is alkyl;
(17) —OPO$_3$H;
(18) —OP(OR$^{15}$)$_2$ wherein R$^{15}$ is as above defined;
(19) —CF$_3$; and
(20) CONH$_2$;
(E) m is 0 or an integer from 1 to 2; and
(F) R$^4$ and R$^5$ are the same and are selected from the group consisting of:
(1) alkyl; and
(2) acyl having the formula —C(O)R$^8$
wherein R$^8$ is selected from the group consisting of H, alkyl, alkenyl, and substituted alkyl;
and wherein
acyl represents a group having the formula —C(O)R$^8$ wherein R$^8$ is selected from the group consisting of H, alkyl, alkenyl, alkynyl, cycloalkyl, cycloalkenyl, and substituted alkyl;
alkenyl represents straight and branched aliphatic hydrocarbon groups having 1 double carbon-to-carbon double bond and having from 2 to 6 carbon atoms;
alkoxy represents an alkyl radical attached to a molecule through an oxygen atom (—O—alkyl);
alkyl represents straight or branched saturated aliphatic hydrocarbon groups having from 1 to 6 carbon atoms;
haloalkenyl represents an alkenyl group, as defined above, wherein one hydrogen atom is replaced by a halogen atom;
alkynyl represents a straight or branched aliphatic hydrocarbon group having one carbon-to-carbon triple bond, and having from 3 to 8 carbon atoms;
cycloalkenyl represents a carbocyclic ring having from 5 to 7 carbon atoms and one carbon-to-carbon double bond in the ring;
cycloalkyl represents a saturated carbocyclic ring having from 3 to 7 carbon atoms;
substituted alkyl represents an alkyl group, as defined above, wherein one of the alkyl H atoms is replaced with a group selected from the group consisting of alkyl, —OH, —O—alkyl, —NH$_2$, —N-(alkyl)$_2$ wherein each alkyl group is the same or different, —S—alkyl, —C(O)O—alkyl, —C(O)H, —NHC(:NH)NH$_2$, —C(O)NH$_2$,—OC(O)NH$_2$, NO$_2$ and —NHC(O)—alkyl, wherein alkyl, is as above defined; and
substituted phenyl represents a phenyl group, as defined above, wherein one or two of the H atoms attached to the ring carbon atoms is replaced by a group independently selected from the group consisting of halo, alkyl, hydroxy, alkoxy, phenoxy, amino, alkylamino, and dialkylamino;
together with the pharmaceutically acceptable salts of the compounds of Formula 1.0 that are acidic or basic.
2. A compound of claim 1 wherein R$^4$ and R$^5$ are acyl.
3. A compound of claim 2 wherein R$^1$ is acyl.

4. A compound of claim 2 wherein $R^1$ is alkyl.

5. A compound of claim 1 wherein $R^2$ is selected from the group consisting of:
   (1) —CH$_3$;
   (2) —OCH$_3$;
   (3) —OCOCH$_3$;
   (4) —OCH$_2$— phenyl;
   (5) Cl;
   (6) F; and
   (7) I.

6. A compound of claim 1 wherein $R^3$ is selected from the group consisting of:
   (1) —CH$_3$;
   (2) —C$_6$H$_{13}$;
   (3) —C$_7$H$_{15}$;
   (4) —CH$_2$-phenyl;
   (5)
   (6) phenyl;
   (7)

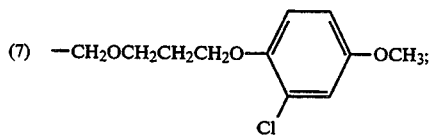

(7) —CH$_2$OCH$_2$CH$_2$CH$_2$O—⟨phenyl with Cl, OCH$_3$⟩

(8) —CH$_2$CO$_2$CH$_2$CH=CH$_2$; and
   (9) —CH$_2$CO$_2$CH$_3$.

7. A compound of claim 1 wherein:
   (B) $R^2$ is selected from the group consisting of:
      (1) —CH$_3$;
      (2) —OCH$_3$;
      (3) —OCOCH$_3$;
      (4) —OCH$_2$-phenyl;
      (5) Cl;
      (6) F; and
      (7) I; and
   (C) $R^3$ is selected from the group consisting of:
      (1) —CH$_3$;
      (2) —C$_6$H$_{13}$;
      (3) —C$_7$H$_{15}$;
      (4) —CH$_2$-phenyl;
      (5)
      (6) —phenyl;

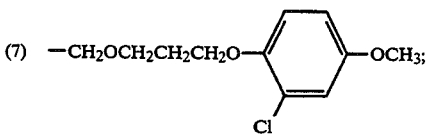

(7) —CH$_2$OCH$_2$CH$_2$CH$_2$O—⟨phenyl with Cl, OCH$_3$⟩

(7)
   (8) —CH$_2$CO$_2$CH$_2$CH=CH$_2$; and
   (9) —CH$_2$CO$_2$CH$_3$.

8. A compound of claim 7 wherein $R^4$ and $R^5$ are acyl and $R^1$ is alkyl.

9. The compound of claim 7 wherein $R^4$, $R^5$ and $R^1$ are the same acyl group.

10. A compound as claimed in claim 1, wherein $R^3$ is selected from from the group consisting of:
    (1) —CH$_3$;
    (2) —C$_6$H$_{13}$;
    (3) —C$_7$H$_{15}$;
    (4) —CH$_2$—phenyl;
    (6) phenyl;

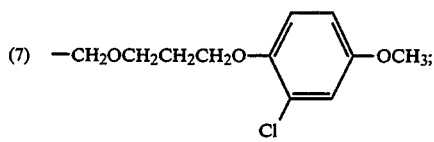

(7) —CH$_2$OCH$_2$CH$_2$CH$_2$O—⟨phenyl with Cl, OCH$_3$⟩

(8) —CH$_2$CO$_2$CH$_2$CH=CH$_2$; and
    (9) —CH$_2$CO$_2$CH$_3$;

$R^2$ is selected from the group consisting of:
    (1) —OH$_3$;
    (2) —OCH$_3$;
    (3) —OCOC H$_3$;
    (4) —OCH$_2$—phenyl;
    (5) Cl;
    (6) F; and
    (7) I; and
    m is 0, 1 or 2;

$R^4$ and $R^5$ are selected from the group consisting of acetyl, 1-oxopentyl, 1-oxopropyl, and methyl; and $R^1$ is selected from the group consisting of methyl, acetyl, 1-oxopentyl, and 1-oxopropyl.

11. A compound as claimed in claim 1, wherein $R^3$ is selected from the group consisting of:
    (1) —CH$_3$;
    (2) —C$_6$H$_{13}$;
    (3) —C$_7$H$_{15}$;
    (4) —CH$_2$—phenyl;
    (5) —CH$_2$CO$_2$CH$_2$CH=CH$_2$;
    (6) —phenyl; and

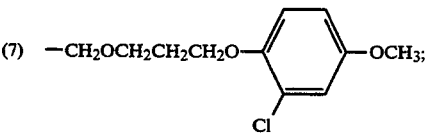

(7) —CH$_2$OCH$_2$CH$_2$CH$_2$O—⟨phenyl with Cl, OCH$_3$⟩

$R^2$ is selected from the group consisting of:
    (1) —CH$_3$;
    (2) —OCOCH$_3$; and
    (3) —OCH$_2$—phenyl; and
    m is 0, 1 or 2;

$R^4$ and $R^5$ are selected from the group consisting of acetyl, 1-oxopentyl, 1-oxopropyl, and methyl; and $R^1$ is selected from the group consisting of methyl, acetyl, 1-oxopentyl, and 1-oxopropyl.

12. A compound selected from the group consisting of

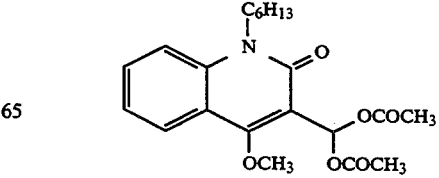

(1.1)

-continued
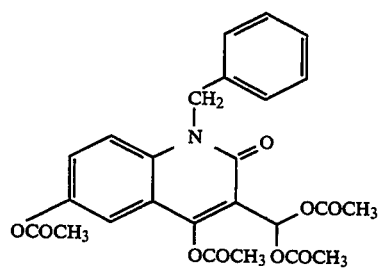 (1.2)
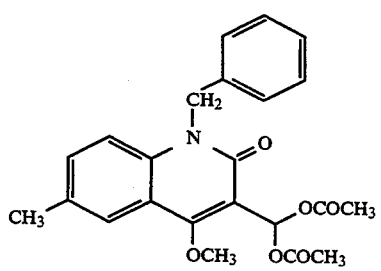 (1.3)
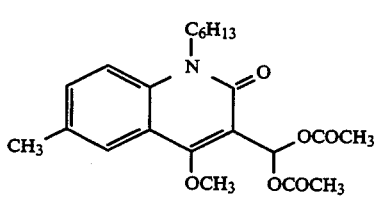 (1.4)
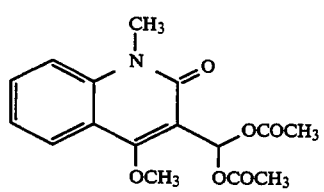 (1.5)
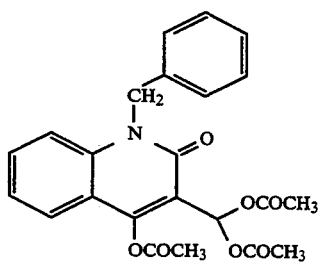 (1.6)
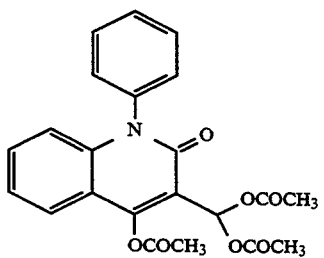 (1.7)
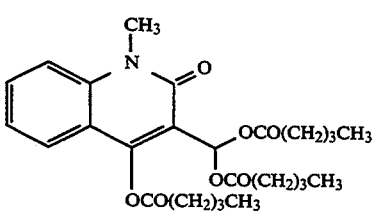 (1.8)
-continued
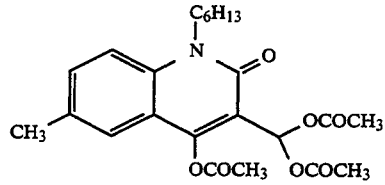 (1.9)
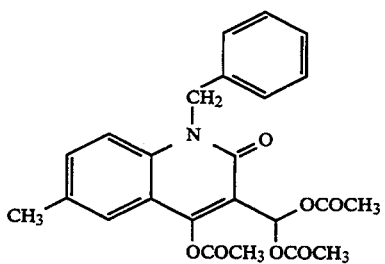 (1.10)
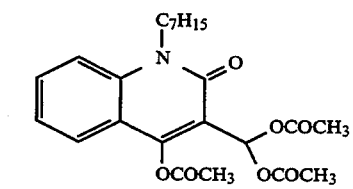 (1.11)
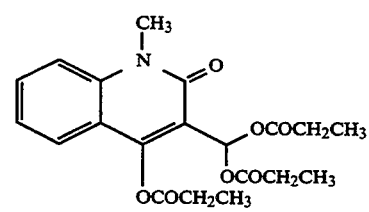 (1.12)
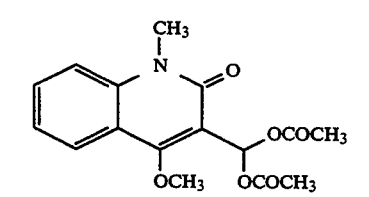 (1.13)
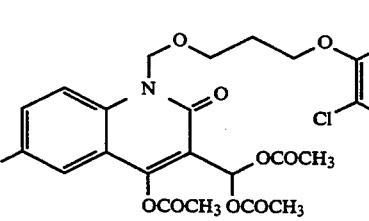 (1.14)
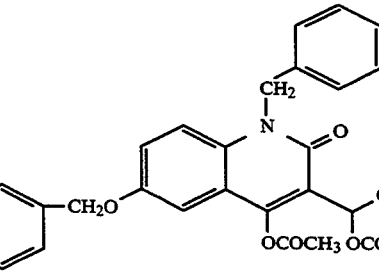 (1.15)

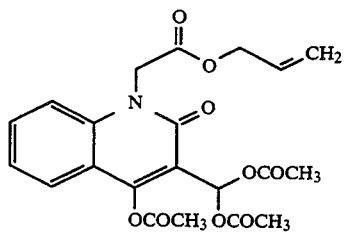
(1.16)

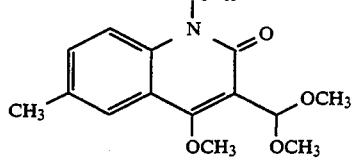
(1.17)

or a pharmaceutically acceptable salt thereof.

13. A pharmaceutical composition comprising an effective amount of a pharmaceutically acceptable carder and an antivirally effective amount of a compound of claim 1.

14. A pharmaceutical composition comprising an effective amount of a pharmaceutically acceptable carder and an antivirally effective amount of a compound of claim 12.

* * * * *